US006261560B1

(12) United States Patent
Tsujinaka et al.

(10) Patent No.: US 6,261,560 B1
(45) Date of Patent: *Jul. 17, 2001

(54) METHOD FOR INHIBITING MUSCLE PROTEIN PROTEOLYSIS WITH ANTIBODIES TO INTERLEUKIN-6 RECEPTOR

(75) Inventors: Toshimasa Tsujinaka, Ikoma; Chikara Ebisui, Ikeda; Junya Fujita, Takatsuki, all of (JP)

(73) Assignee: Chugai Seiyaku Kabushiki Kaisha, Tokyo (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/875,927

(22) PCT Filed: Feb. 13, 1996

(86) PCT No.: PCT/JP96/00310

§ 371 Date: Aug. 13, 1997

§ 102(e) Date: Aug. 13, 1997

(87) PCT Pub. No.: WO96/25174

PCT Pub. Date: Aug. 22, 1996

(30) Foreign Application Priority Data

Feb. 13, 1995 (JP) .................................................... 7-046587
Nov. 30, 1995 (JP) .................................................... 7-334356

(51) Int. Cl.[7] .................................................. A61K 39/395
(52) U.S. Cl. .................................... 424/143.1; 424/130.1; 424/139.1; 424/141.1; 424/142.1; 514/907; 514/921; 530/387.1; 530/387.9; 530/388.1; 530/388.22
(58) Field of Search .............................. 424/130.1, 139.1, 424/141.1, 142.1, 143.1, 145.1; 514/907, 921; 530/387.1, 387.9, 388.1, 388.22

(56) References Cited

FOREIGN PATENT DOCUMENTS 9219757    12/1992   (WO) .

OTHER PUBLICATIONS

Cannon et al. The American Physiological Society, vol. 260, No. 6, pt. 2 pp. R1235–1240, 1991.

Tamura et al. (1993) Proc. Natl. Acad. Sci. USA, vol. 90, pp. 11924–11928.

Mirata et al. (1989) vol. 143, pp. 2900–2906, No. 9, The Journal of Immunology.

Goodman. Proceedings of the Society for Experimental Biology & Medicine, (1994) vol. 205, No. 2, pp. 182–185.

Natanson et al. (1994) Annals of Internal Medicine, vol. 120, No. 9, pp. 771–783, May 1, 1994.*

Ebisui et al., "Interleukin–6 induces proteolysis by activating intracellular proteases (cathepsins B and L, proteasome) in C2C12 Myotubes" *Clinical Science* 89:431–439 (1995.

Tsujinaka et al., "Interleukin 6 Receptor Antibody Inhibits Muscle Atrophy and Modulates Proteolytic Systems in Interleukin 6 Transgenic Mice" *J. Clinic Invest.* 97:244–249 (1996).

Fujita et al., "Anti–Interleukin–6 Receptor Antibody Prevents Muscle Atrophy in Colon–26 Adenocarcinoma–Bearing Mice with Modulation of Lysosomal and ATP–Ubiquitin–Dependent Proteolytic Pathways"*Int. J. Cancer* 68, pp. 637–643 (1996).

Miyai et al., Proc. Jpn. Soc. Immunol vol.21 (1991) (English Translation).

Fujita et al., "Official Journal of the European Society of Parenteral and Enteral Nutrition" *Clinical Nutrition* Supplement 2 vol. 14 p. 15 (1995).

Yano et al., "Official Journal of the European Society of Parenteral and Enteral Nutrition" *Clinical Nutrition* Supplement 2 vol.14 p.66 (1995).

Fujita et al., ASPEN 20th Clinical Congress No. 8 (1996).

Yano et al., ASPEN 20th Clinical Congress No. 89 (1996).

* cited by examiner

*Primary Examiner*—Prema Mertz
(74) *Attorney, Agent, or Firm*—Foley & Lardner

(57) ABSTRACT

The present invention provides a muscle protein proteolysis inhibiting agent comprising antibody to Interleukin-6 receptor (IL-6R antibody). Antibodies of animals other than humans such as mice and rats, chimeric antibodies of these antibodies with human antibodies, and reshaped human antibodies and so forth can be used for the IL-6R antibody. The muscle protein proteolysis inhibiting agent of the present invention is useful in the inhibition of muscle protein proteolysis observed in diseases such as cancerous cachexia, sepsis, serious trauma or muscular dystrophy.

13 Claims, 13 Drawing Sheets

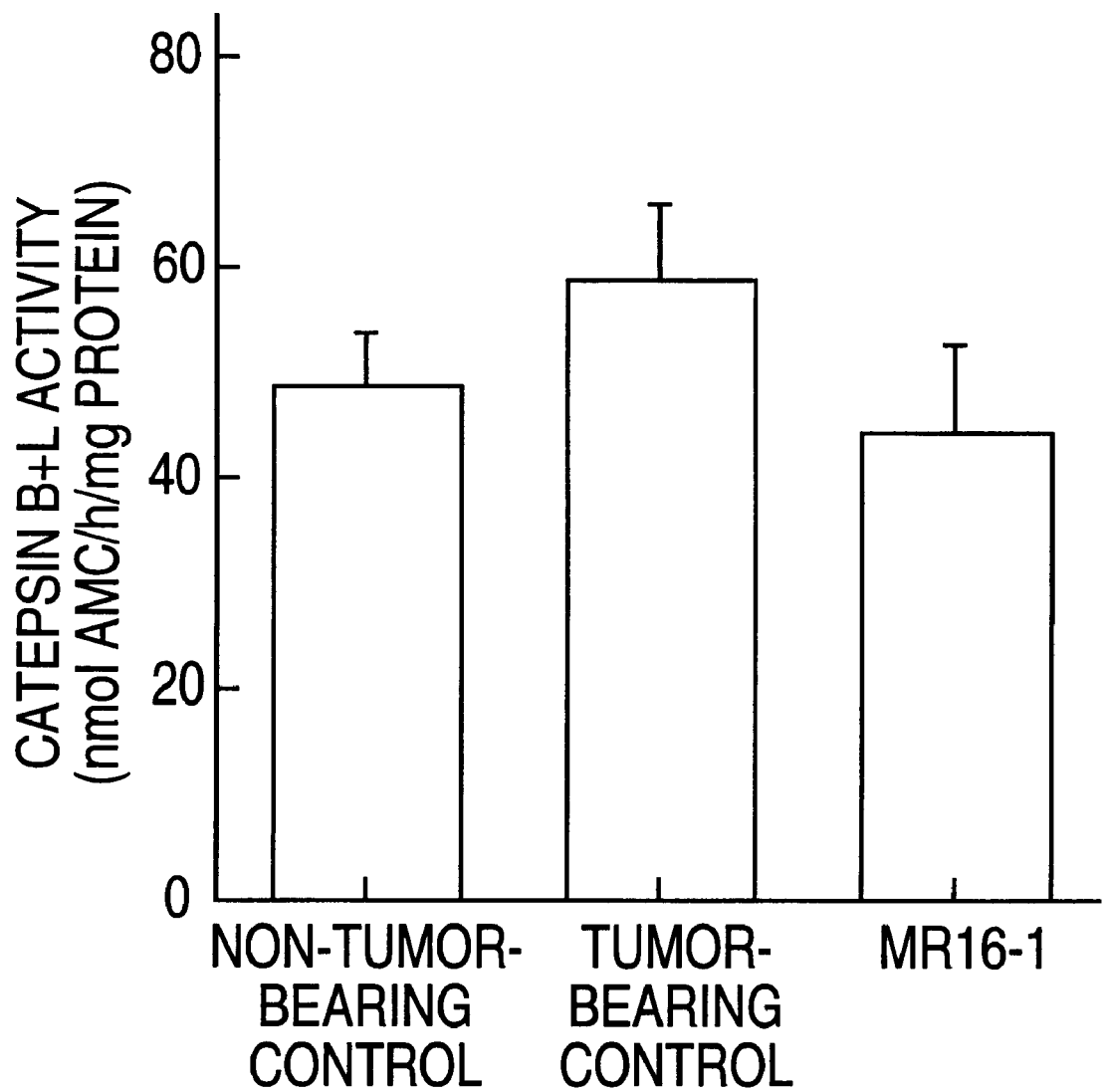

METHOD FOR INHIBITING MUSCLE PROTEIN PROTEOLYSIS WITH ANTIBODIES TO INTERLEUKIN-6 RECEPTOR

CROSS REFERENCE TO RELATED APPLICATION

This is a national stage application under 35 U.S.C. 371 of PCT application PCT/JP96/00310, filed Feb. 13, 1996.

TECHNICAL FIELD

The present invention relates to a muscle protein proteolysis inhibiting agent comprising antibody (anti-IL-6R) to Interleukin-6 receptor (IL-6R)

BACKGROUND ART

IL-6 is a cytokine generically referred to as B cell stimulating factor 2 or Interferon β2. IL-6 was discovered to be a differentiation factor involved in activation of B lymphocytic cells (Hirano, T. et al., Nature 324, 73–76, 1986). Later, it was shown to have an effect on the functions of various cells (Akira, S. et al., Adv. in Immunology 54, 1–78, 1993).

IL-6 is a multi-functional cytokine that acts at various stages of immunity, hematopoiesis, acute phase reactions and so forth (Taga, T. et al., Critical Reviews in Immunol. 1992; 11: 265–280), and in addition to acting as a growth factor of multiple myeloma, has also been reported to be involved in various diseases such as illneses in which plasmacytosis is observed including rheumatism (Hirano, T. et al., Eur. J. Immunol. 1986; 18: 1797–1801; Houssiau, F. A. et al., Arth. Rheum. 1988; 31: 784–788) and Castleman's disease (Yoshizaki, K. et al., Blood 1989; 74: 1360–1367; Brant, S. J. et. al., Clin. Invest. 1990; 86: 592–599), or mesangial cell proliferative nephritis (Ohta, K. et al., Clin. Nephrol. (Germany) 1992; 38 185–189; Fukatsu, A. et al., Lab. Invest. 1991; 65: 61–66; Horii, Y. et al., J. Immunol. 1989; 143: 3949–3955) and cachexia accompanying tumor growth (Strassman, G. et al., J. Clin. Invest. 1992; 89: 1681–1684).

In H-2Ld hIL-6 transgenic mice (IL-6 Tgm), in which human IL-6 (hIL-6) was expressed in excess by genetic engineering, IgG1 plasmacytosis, mesangium proliferative nephritis, anemia, thrombocytopenia and the appearance of autoantibodies were observed (Miyai, T. et al., 21st Japan Immunol. Soc. Pres. "Hematological and Serological Changes Accompanying Aging in H-2Ld hIL-6 Transgenic Mice": 1991), thereby suggesting that IL-6 is involved in various diseases.

In addition, IL-6 is also known to have the effect of promoting muscle protein proteolysis in myoblasts in vitro (Ebisui, T. et al., Clinical Science, 1995; 89: 431–439).

However, it has heretofore been unknown that antibody to interleukin-6 receptor is effective in inhibiting proteolysis of muscle proteins, and such attempts have yet to be made.

DISCLOSURE OF THE INVENTION

The present invention is intended to provide a drug that inhibits proteolysis of muscle proteins, and more particularly, provides a muscle protein proteolysis inhibiting agent comprising antibody to IL-6 receptor.

Following the occurrence of cancerous cachexnia, septicemia, serious trauma or muscular dystrophy and so forth, proteolysis of skeletal muscle protein proceeds so that a decrease in muscle mass is observed. Until now, only nosotropic measures were implemented for inhibiting agents of this muscle protein proteolysis in these diseases, and a fundamental method of treatment for these diseases has yet to be established.

As a result of conducting earnest studies on the effects of IL-6 receptor antibody on proteolysis of skeletal muscle proteins, the inventors of the present invention found that IL-6 receptor antibody inhibits the expression of proteolytic enzyme systems that promote muscle protein proteolysis as well as their activity, thereby leading to completion of the present invention.

Namely, the present invention relates to a muscle protein proteolysis inhibiting agent comprising IL-6 receptor antibody.

BRIEF DESCRIPTION OF THE DRAWINGS

FIG. 13 is a graph indicating cathepsin B+L activity in mouse gastroenemius muscle on experiment day 17.

DETAILED DESCRIPTION

Figure 1:
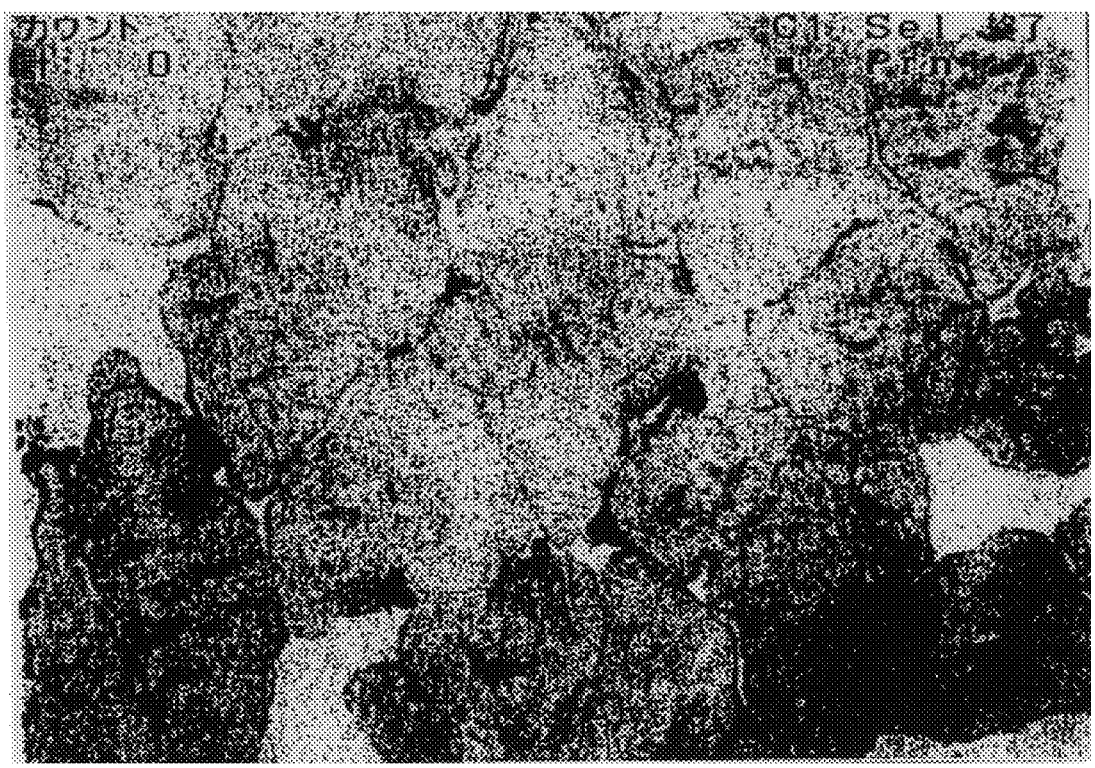
FIG. 1 is a photograph that shows the results of immunostaining with cathepsin B of a piece of gastroenemius muscle tissue obtained from a control mouse (x400).
Figure 2:
FIG. 2 is a photograph that shows the results of immunostaining with cathepsin B of a piece of gastroenemius muscle tissue of an IL-b 6transgenic mouse administered PBS (x400).
Figure 3:
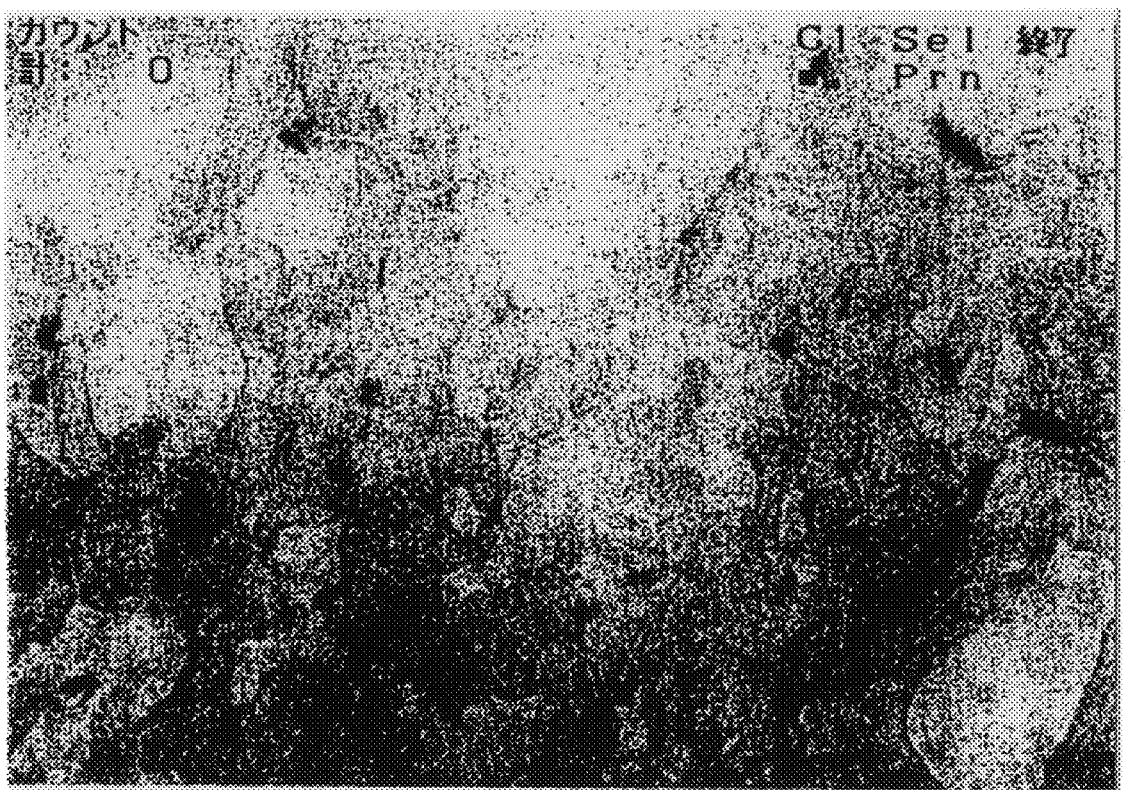
FIG. 3 is a photograph that shows the results of immunostaining with cathepsin B of a piece of gastroenemius muscle tissue of an IL-6 transgenic mouse administered IL-6 receptor antibody (x400).
Figure 4:
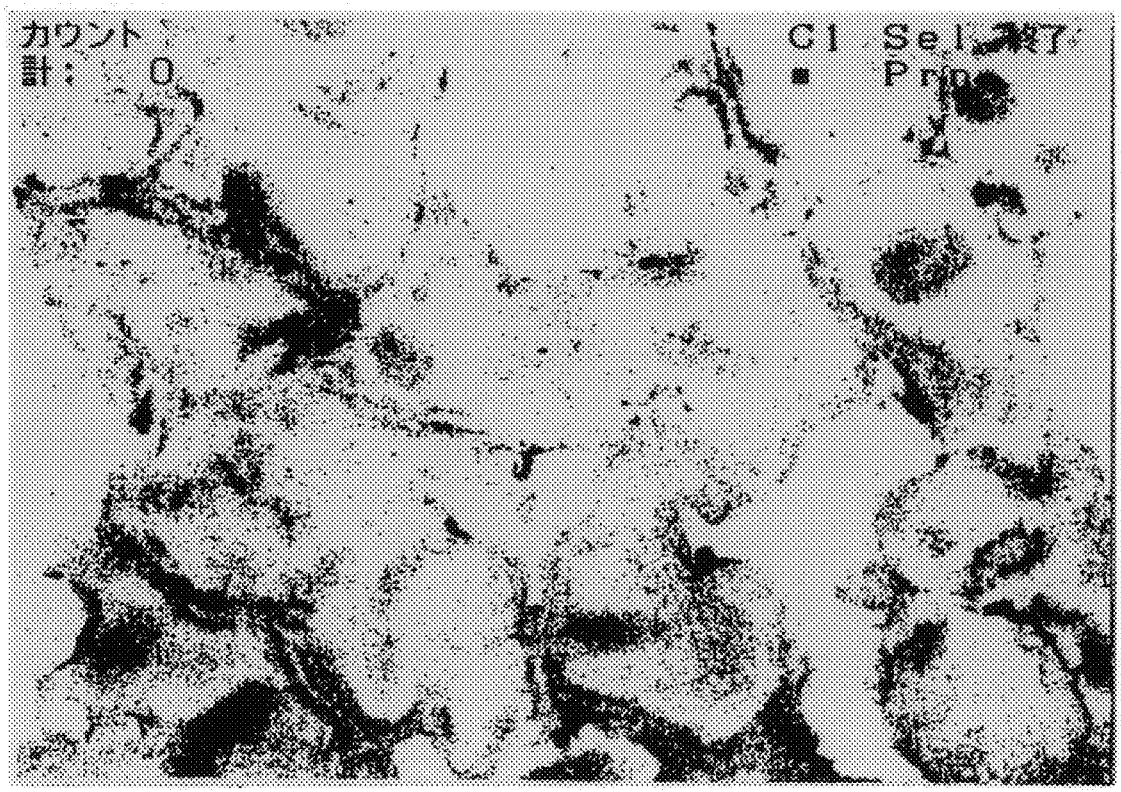
FIG. 4 is a photograph that shows the results of immunostaining with cathepsin L of a piece of gastroenemius muscle tissue obtained from a control mouse (x400).
Figure 5:
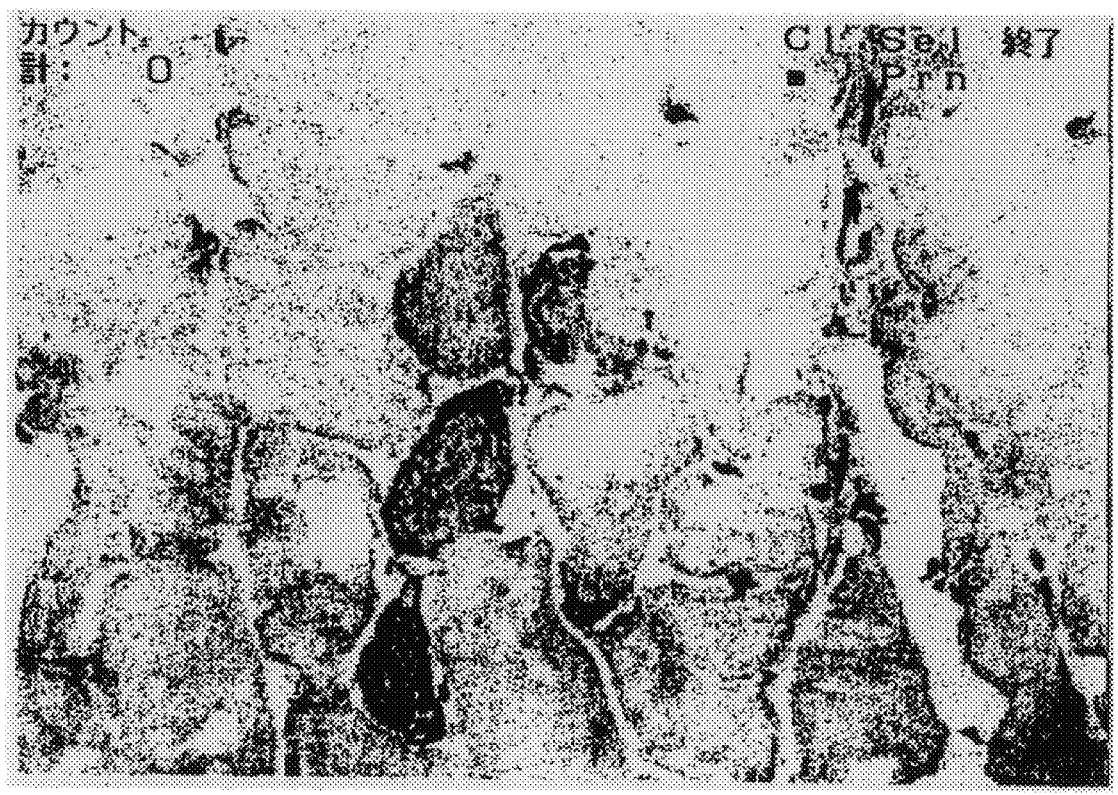
FIG. 5 is a photograph that shows the results of immunostaining with cathepsin L of a piece of gastroenemius muscle tissue of an IL-6 transgenic mouse administered PBS.
Figure 6:
FIG. 6 is a photograph that shows the results of immunostaining with cathepsin L of a piece of gastroenemius muscle tissue of an IL-6 transgenic mouse administered IL-6 receptor antibody (x400).

The muscle protein proteolysis inhibiting agent of the present invention inhibits breakdown of skeletal muscle and prevents decrease in muscle mass by decreasing the expression and activity of proteolytic enzyme systems induced or enhanced by IL-6. The proteolytic enzyme systems referred to here indicate lysosomal and non-lysosomal proteolysis pathways such as those of cathepsin B or L and ubiquitin.

Examples of diseases in which muscle protein proteolysis is inhibited and decreases in muscle mass are prevented by the muscle protein proteolysis inhibiting agent of the present invention include cancerous cachexia, sepsis, serious trauma and muscular dystrophy.

Although the IL-6 receptor antibody used in the present invention may be of any origin or type (monoclonal or polygonal) provided it blocks signal transduction by IL-6 and inhibits biological activity of IL-6, monoclonal antibody of mamalian origin is particularly preferable. As a result of binding with IL-6R, this antibody inhibits binding between IL-6 and IL-6R, thereby blocking signal transduction of IL-6 and inhibiting the biological activity of IL-6.

There are no particular limitations on the animal species of monoclonal antibody-producing cells provided it is mammalian, and the antibody may be human antibody or that derived from mammalian cells other than human cells. In the case of monoclonal antibody derived from mammalian cells other than human cells, monoclonal antibody of rabbits or rodents is preferable due to the case of their production. Although there are no particular limitations on the type of rodent cells used, preferable examples include mouse, rat and hamster cells.

Particularly preferable examples of this type of IL-6 receptor antibody include MR16-1 antibody (Tamura, T. et al., Proc. Natl. Acad. Sci. U.S.A. 90, 11924–11928, 1993) and PM-1 antibody (Hirata, Y. et al., J. Immunol. 143, 2900–2906, 1989). The hybridoma MR16-1 was deposited as FERM BP-5875 on Mar. 13, 1997, and hybridoma PM-1 was deposited as FERM BP-2998 on Jul. 10, 1990, both as international deposits under the Budapest Treaty at the National Institute of Bioscience and Human-Technology, Agency of Industrial Science and Technology, Ministry of International Trade and Industry, 1-3, Higaski 1-chrome, Tsukuba-shi Ibaraki-ken, 305, Japan.

Monoclonal antibody can basically be prepared in the manner shown below using known techniques. Namely, using IL-6R as the sensitizing antigen, a host is immunized with this sensitizing agent in accordance with a routine immunization method, after which the resulting immune cells are fused with known parent cells according to routine cell fusion methods, followed by screening for monoclonal antibody-producing cells using ordinary screening methods.

More specifically, the following procedure should be followed to prepare monoclonal antibody. For example, the above-mentioned sensitizing antigen is obtained by using the gene sequence of human IL-6R disclosed in European Patent No. EP325474. After inserting the gene sequence of human IL-6R into a known expression vector system and transforming a suitable host cell, the target IL-6R protein is purified from the host cell or culture supernatant, after which this purified IL-6R protein is used as the sensitizing antigen.

In addition, the above-mentioned sensitizing antigen of mouse origin is obtained by using the gene sequence of mouse IL-6R disclosed in Japanese Unexamined Patent Publication No. 3-155795, and following the same procedure as that using the gene sequence of human IL-6R described above.

In addition to that which is expressed on the cell membrane, IL-6R capable of being released from the cell membrane (sIL-6R) can also be used as antigen. sIL-6R is composed mainly of the extracellular region of the IL-6R bound to the cell membrane, and differs from membrane-bound IL-6R in that it is deficient in a transmembrane region, or a transmembrane region and an intracellular region.

Although there are no particular limitations on mammals that are immunized with a sensitizing antigen, it is preferable to select a mammal in consideration of compatability with the parent cells used for cell fusion. Typical examples of mammals used include mice, rats, hamsters and rabbits.

Immunizations of the animal with the sensitizing antigen is performed in accordance with known methods. For example, as a example of a typical method, immunization can be performed by injecting the sensitizing antigen either intraperitoneally or subcutaneously. More specifically, after diluting and suspending the sensitizing antigen in a suitable amount of phosphate-buffered saline (PBS) or physiological saline, the resulting suspension is mixed with a suitable amount of an ordinary adjuvant, such as Freund's complete adjuvant, as necessary. Following emulsification, the resulting emulsion is suitable administered to the mammal over the course of several administrations every 4 to 21 days. In addition, a suitable carrier can be used during immunization with the sensitizing antigen.

After immunizing in this manner and confirming that the level of the desired antibody has risen in the serum, immune cells are removed from the mammal and used for cell fusion. Preferable examples of immune cells are spleen cells in particular. The myeloma cells of a mammal used as the other parent cells to be fused with above-mentioned immune cells can be various previously known cell strains, preferable examples of which include P3 (P3x63Ag8.653) (J. Immunol. 123: 1458, 1978), P3-UI (Current Topics in Microbiology and Immunology 81: 1–7, 1978), NS-1 (Eur. J. Immunol. 6: 511–519, 1976), MPC-11 (Cell, 8: 405–415, 1976), SP2/0 (Nature, 276: 269–270, 1978), OF (J. Immunol. Meth. 35: 1–21, 1980), S194 (J. Exp. Med. 148: 313–323, 1978) and R210 (Nature, 277: 131–133, 1979).

Cell fusion of the above-mentioned immune cells and myeloma cells can basically be performed according to known methods, such as the method of Milstein, et al. (Millstein, et al., Methods Enzymol. 73: 3–46, 1981). More specifically, the above-mentioned cell fusion is carried out during the course of ordinary nutrient culturing in the presence of a cell fusion promoter. Examples of fusion promoters that are used include polyethyleneglycol (PEG) and Sendai virus (HVJ). Moreover, an assistant such as dimethylsulfoxide can be added and used to improve fusion efficiency as desired.

The ratio of immune cells and myeloma cells used are preferably, for example, 1 to 10 times immune cells to myeloma cells. RPMI1640 culture medium and MEM culture medium suitable for growth of the above-mentioned myeloma cell strain as well as other ordinary culture medium used in this type of cell culturing can be used for the culture medium used for the above-mentioned cell fusion. Moreover, this can also be used in combination with serum supplements such as fetal calf serum (FCS).

For this cell fusion, the prescribed amounts of the above-mentioned immune cells and myeloma cells are mixed well in the above-mentioned culture medium followed by the addition of a PEG solution warmed in advance to about 37° C., for example a PEG solution having a mean molecular weight of about 1000 to 6000, normally at a concentration of 30 to 60% (w/v) and mixing to form the target fused cells (hybridoma). Continuing, by sequentially adding a suitable amount of culture medium and repeating centrifugation and removal of supernatant, cell fusion agents and so forth not suitable for hybridoma growth can be removed.

Said hybridoma is selected by culturing in an ordinary selective culture medium such as HAT culture medium (culture medium containing hypoxanthine, aminopterin and thymidine). Culturing in said HAT culture medium is usually contained for several days to several weeks or for an amount of time that is sufficient for eliminating all cells other than the target hybridoma (non-fused cells). Next, screening and single-cloning of hybridoma that produces the target antibody is performed by carrying out ordinary limiting dilution.

The hybridoma thus prepared that produces monoclonal antibody can be subcultured in ordinary culture medium, and stored for a long time in liquid nitrogen.

In order to acquire monoclonal antibody from said hybridoma, said hybridoma is cultured in accordance with ordinary methods and a method is employed for obtaining in the form of culture supernatant, or a method is employed in which the hybridoma is transplanted into a mammal with which it is compatible, allowed to grow and then antibodies are obtained in the form of ascites. The former method is suitable for obtaining highly pure antibody, while the latter method is suitable for large-amount production of antibody.

In addition, monoclonal antibody is not only obtained from antibody-producing cells obtained by immunizing with antigen or from a hybridoma produced by cell fusion, but monoclonal antibody can also be used that is produced using gene recombination technology by cloning an antibody gene, incorporating that gene into a suitable vector, and introducing that vector into a known cell strain such as COS or CHO cells (see, for example, Vandamme, A-M et al., Eur. J. Biochem., 192, 767–775, 1990).

Moreover, the monoclonal antibody obtained by using the above-mentioned methods can be purified to high purity by utilizing ordinary purification techniques such as salt precipitation, gel filtration or affinity chromatography. Monoclonal antibody produced in this manner can be confirmed to recognize antigen both at high sensitivity and high accuracy by ordinary immunological techniques such as radioimmunoassay (RIA), enzyme immunoassay (EIA, ELISA) and immunofluorescence analysis.

The monoclonal antibody used in the present invention is not limited to monoclonal antibody produced by hybridoma, but may also be that which has been antifincially modified for the purpose of lowering heteroantigenicity to humans. For example, chimeric antibody can be used that is composed of the variable regions of the monoclonal antibody of a mouse or other mammal other than a human and constant regions of human antibody. This type of chimeric antibody can be produced using known methods for producing chimeric antibody, and particularly gene recombination technology.

Moreover, reshaped human antibody can also be used in the present invention. Reshaped antibody is that in which the complementarity determining regions of a human antibody is replaced with the complementarity determining regions of an antibody of a mammal other than human such as a mouse, and its general gene recombination techniques are known. A reshaped human antibody that is useful in the present can be obtained by using these known methods.

Furthermore, amino acids of the framework (FR) regions of the variable region of antibody may be substituted so as to form a suitable antigen binding site in the complementarity determining regions of reshaped human antibody (Sato, et al., Cancer Res. 53: 1–6, 1933). A preferable example of this type of reshaped human antibody is humanized PM-1 (hPM-1) (see International Patent Application No. WO92-19759).

Moreover, a gene can be constructed that codes for antibody fragments, such as Fab or Fv, or a single chain Fv (scFv) in which Fv of the H chain and L chain are connected with a suitable linker, this gene can then be expressed in a suitable host cell and then used for the purpose described above, provided it binds to antigen and inhibits the activity of IL-6 (see, for example, Bird, et al., TIBTECH, 9: 132–137, 1991; Huston, et al., Proc. Natl. Acad. Sci. USA, 85, 5879–5883, 1988). Moreover, the V region of the above-mentioned reshaped antibody can be used for the Fv of the H chain and L chain used for producing scFv.

The muscle protein proteolytic enzyme inhibiting agent comprising IL-6 receptor antibody of the present invention can be used in the present invention provided it blocks signal transduction of IL-6, and is effective against diseases exhibiting breakdown of muscle protein. The preventive therapeutic drug of the present invention is preferably administered parenterally, and can be administered systemically or topically by, for example, intravenous injection, intramuscular injection, intraperitoneal injection or subcutaneous injection. Moreover, it can also take on the form of a pharmaceutical composition or kit with at least one type of pharmaceutical vehicle or diluent.

Although varying according to patient condition and age or by the method of administration, it is necessary to select a suitable dose for the dose of the preventive or therapeutic drug of the present invention for human. For example, a dose divided among four administrations or less within the range of about 1 to 1000 mg/patient can be selected. In addition, it can be administered at a dose of 1 to 10 mg/kg/week. However, the preventive or therapeutic drug of the present invention is not limited to these doses.

The preventive or therapeutic drug of the present invention can be prepared in accordance with routine methods. For example, to prepare an injection preparation, purified IL-6R antibody is dissolved in a solvent such as physiological saline or buffer, followed by the addition of an adsorption preventive such as Tween80, gelatin or human serum albumin (HSA). Alternatively, it may also be freeze-dried in order to be reconstituted prior to use. Examples of vehicles that can be used for freeze-drying include sugar alcohols and sugars such as mannitol and glucose.

EXAMPLES

Although the following provides a detailed explanation of the present invention through its reference examples and examples, the present invention is not limited to them.

Reference Example 1

Preparation of B6Ld-IL-6

Transgenic Mice

A 3.3 kb Sph1-XhoI1 fragment containing human IL-6 cDNA fused with H-2Ld promtoer (Ld-IL-6) (Suematsu, et al., Proc. Natl. Acad. Sci. U.S.A., 86, 7547, 1989) was injected by microinjection into the pronucleus of the fertilized ovum from C57BL/6J (B6) mice (Japan Clea) in accordance with the method of Yamamura, et al. described in J. Biochem. 96, 357, 1984.

Introduction of the above-mentioned trans-gene was screened by southern blot analysis of EcoRI-digested caudal DNA using a $^{32}$P-labeled TaqI-BanII fragment of human IL-6 cDNA for the probe. The trans-gene was detected by identifying the transgenic mice by PCR analysis of caudal DNA using TaqDNA polymerase and two types of primers specific for human IL-6 cDNA, namely CHIL6P5 (5'-ACCTCTTCAGAACGAATTGACAAA-3') (SEQ ID NO:

1) and CHIL6P7i (5'-AGCTGCGCAGAATGAGATGAGTTGT-3') (SEQ ID NO: 2). The serum IL-6 concentrations as determined by human IL-6 specific ELISA (Matsuda, T. et al., Eur. J. Immunol., 18, 951–956, 1988) in these transgenic mice were higher than 600 pg/ml after 12 weeks of age.

Referance Example 2
Preparation of Rat Anti-IL-6R
Antibody

Mouse soluble IL-6R-producing CHO cells were prepared as described in Saito, et al., J. Immunol. 147, 168–173, 1991. These cells were cultured in aMEM containing 5% fetal bovine serum (FBS) at 37° C. in a humid atmosphere containing 5% $CO_2$ in air. The conditioned medium was recovered and used as an sIL-6R preparation. The concentration of mouse sIL-6R in the medium was measured by sandwich ELISA using monoclonal anti-mouse IL-6R antibody RS15 (Saito, et al., J. Immunol. 147, 168–173, 1991) and rabbit polyclonal anti-mouse IL-6R antibody.

The mouse sIL-6R was purified by an affinity column to which was adsorbed monoclonal anti-mouse IL-6R antibody (RS12). Wistar rats were immunized by subcutaneous injection of 50 μg of purified mouse sIL-6R in Freund's complete adjuvant, followed by boosting with four injections of 50 μg of mouse sIL-6R in Freund's incomplete adjuvant once a week starting two weeks later. One week after the final boosting, the rats were intravenously administered with 50 μg of mouse sIL-6R in 100 μl of phosphate buffered saline (PBS).

The spleens were removed from the rats 3 days later, and the rat spleen cells were fused with mouse p3U1 myeloma cells at a ratio of 10:1 using polyethyleneglycol (Boehringer-Manheim). After incubating overnight in 100 μl of RPMI1640 medium containing 10% FBS at 37° C. in wells of a 96-well plate (Falcon 3075), 100 μl of hypoxanthine, aminopterin and thymidine (HAT) medium containing human IL-6 were added to each well. Half of the medium was replaced with HAT medium daily for 4 days.

After 7 days, hybridoma that produced anti-mouse sIL-6R were selected by mouse sIL-6R binding assay (ELISA). In other words, 100 μl of hybridoma supernatant were incubated for 60 minutes in plates coated with rabbit polyclonal anti-rat IgG antibody at 1 μg/ml. The plates were then washed and incubated with 100 μg/ml of mouse sIL-6R. After washing, rabbit polyclonal anti-mouse IL-6R antibody was added at 2 μg/ml after which the plates were washed followed by incubation for 60 minutes with alkaline phosphatase-linked goat polyclonal anti-rabbit IgG antibody (Tago).

Finally, after washing, the plates were incubated with alkaline phosphtase substrate (Sigma 104; p-nitrophenylphosphate) and then read using a plate reader (Tosoh) at 405 nm. Hybridoma that recognized mouse sIL-6R was cloned twice by limited dilution. In order to prepare the ascites, 0.5 ml of pristane was injected twice into BALB/c nu/nu mice, after which $3 \times 10^6$ of established hybridoma cells were injected intraperitoneally 3 days later. The ascites were collected 10 to 20 days later, and monoclonal antibody MR16-1 was purified from the ascites using a protein G column (Oncogene Science).

The neutralizing effect on IL-6 by antibody produced by MR16-1 was tested according to uptake of $^3$H-thymidine by MH60.BSF2 cells (Matsuda, et al., Eur. J. Immunol. 18: 951–956, 1988). MH60.BSF2 cells were distributed in a 96-well plate in an amount of $1 \times 10^4$ cells/200 μl/well followed by the addition of mouse IL-6 (10 pg/ml) and MR16-1 or RS12 antibody after which the cells were cultured for 44 hours in 5% $CO_2$ at 37° C. Next, $^3$H-thymidine (1 mci/well) was added to each well and uptake of 3H-thymidine was measured 4 hours later.

Example 1

Experiment 1

Transgenic mice prepared as described above were kept in individual cages in an air-conditioned room set to a light/dark cycle of 12 hours per day. The animals were fed ad-lib with standard laboratory diet CE-2 obtained from Japan Clea. For the control, normal C57BL/6J mice were kept under the identical conditions. The mice were assigned to three groups. Six of the normal mice were assigned to the control group (C-1 through C-6, all females). Six of the above-mentioned transgenic mice were asigned to the test groups (A-1 through A-4=females, A-5 and A-6; males). Five of the above-mentioned transgenic mice were assigned to a comparison group (P-1 through P-4=females, P-5= male).

After keeping until 4 weeks old, the mice of the test group were intravenously administered with mouse monoclonal antibody MR16-1 to IL-6 receptors described in Reference Example 2 at a dose of 2 mg/mouse at 5 weeks old. The above-mentioned mouse monoclonal antibody MR16-1 was then administered subcutaneously twice a week at a dose of 100 μg/mouse from 6 to 14 weeks of age. After weighing the mice at 15 weeks old, the mouse were autopsied to remove gastroenemius muscle and the spleen after which their weights were measured. the gastroenemius muscle samples were rapidly frozen in liquid nitrogen after measurement of weight. In the comparison group, the animals were managed simultaneous to the test group with the exception of administering an equal volume of phosphate buffered saline (PBS) instead of antibody. The animals of the control were administered with neither antibody nor PBS.

Those results are as shown in Table 1.

TABLE 1

| | | Body weight (g) | | | Gastrocnemius muscle weight (mg) | | | Spleen weight (mg) | | |
|---|---|---|---|---|---|---|---|---|---|---|
| Mouse | Sex | Wgt. | Mean | S.D. | Wgt. | Mean | S.D. | Wgt. | Mean | S.D. |
| C-1 | F | 21.67 | | | 131.9 | | | 964 | | |
| C-2 | F | 19.77 | | | 112.8 | | | 877 | | |
| C-3 | F | 21.58 | | | 127.8 | | | 911 | | |
| C-4 | F | 20.31 | | | 112.1 | | | 864 | | |
| C-5 | F | 18.58 | | | 110.1 | | | 823 | | |
| C-6 | F | 21.11 | 20.5 | 1.2 | 121.2 | 119.3 | 9.09 | 738 | 862.8 | 77.4 |
| P-1 | F | 23.84 | | | 91.8 | | | 1303 | | |

TABLE 1-continued

| Mouse | Sex | Body weight (g) | | | Gastrocnemius muscle weight (mg) | | | Spleen weight (mg) | | |
|---|---|---|---|---|---|---|---|---|---|---|
| | | Wgt. | Mean | S.D. | Wgt. | Mean | S.D. | Wgt. | Mean | S.D. |
| P-2 | F | 18.07 | | | 71.8 | | | 1061 | | |
| P-3 | F | 21.19 | | | 109.1 | | | 977 | | |
| P-4 | F | 23.68 | 21.7 | 2.7 | 91.3 | 91.0 | 15.2 | 1628 | 1242 | 292 |
| P-5 | M | 30.56 | | | 192.1 | | | 1722 | | |
| A-1 | F | 20.09 | | | 110.1 | | | 921 | | |
| A-2 | F | 19.6 | | | 121.8 | | | 868 | | |
| A-3 | F | 18.15 | | | 106.9 | | | 843 | | |
| A-4 | F | 21.03 | 19.7 | 1.2 | 130.4 | 117.3 | 10.8 | 902 | 888.5 | 33.2 |
| A-5 | M | 23.52 | | | 144.2 | | | 1032 | | |
| A-6 | M | 23.60 | 23.6 | 0.06 | 139.7 | 142.0 | 3.18 | 1049 | 1041 | 12 |

Despite the body weights of the comparison group being higher than the control group, gastroenemius muscle weights were lower and muscle atrophy was observed. In addition, increase in spleen weight was also observed. On the other hand, these changes were not observed in the test group, and results were nearly the same as those in the control group for all parameters.

Experiment 2

Animals were kept and managed in the same manner as Experiment 1. Six of the above-mentioned normal mice (C-1 through C-6=all females) were assigned to the control group, and five of the above-mentioned transgenic mice (A-1 through A-4=females, A-5=male) were assigned to the test group. Five of the above-mentioned transgenic mice (P-1 through P-4=females, P-5 through P-6=males) were assigned to the comparison group. Mouse gastroenemius muscle obtained at 16 weeks old in the same manner as Experiment 1 was washed twice with a homogenization solution (250 mM sucrose, 2 mM EGTA, 2 mM EDTA, 20 mM Tris-HCl, pH 7.4) followed by homogenization to prepare a cell suspension using a polytron homogenizer and ultrasonic treatment in 1 ml of the above-mentioned homogenization solution containing 0.2% Triton-X100.

The resulting homogenate was separated by centrifuging for 15 minutes at 18,000 G. The supernatant was diluted with an equal volume of glycerol and stored at −40° C. until the time of analysis. Cathepsin B activity was then assayed at pH 6.0 using as substrate 10 $\mu$M Z-Arg-Arg-AMC in accordance with the method of Barrett, et al. (Barrett, A. J. et al., Methods Enzymol., 80, 535–561, 1976). Separate from this, in order to obtain a blank sample, the above-mentioned extract was incubated for 5 minutes at 37° C. with 1 $\mu$M E-64 (L-3-carboxy-trans-2,3-epoxypropionyl-leucylamido-(4-guanidino)butane) (Protein Research Foundation, Osaka) to inhibit cathepsin B activity.

Cathepsin B+L activity was assayed in the same manner as assay of cathepsin B activity with the exception of using Z-Phe-Arg-Amc as the substrate. Since this substrate is hydrolyzed not only by cathepsin L, but also by cathepsin B, its hydrolysis can be sued as an indicator of cathepsin B+L activity. The protein concentration of the extract was determined according to the method of Bradford (Bradford, M. M., Anal. Biochem., 72, 248–254, 1976).

Specific activity (nmol AMC/mg protein hour) was calculated for each animal by dividing the rate of AMC production in the above-mentioned assay (nmol AMC/ml hr) by protein concentration (mg/ml). Those results are shown in Tables 2 and 3.

TABLE 2

Cathepsin B

| Mouse | Δ AMC | Protein Conc. | Specific Activity | Mean | S.D. |
|---|---|---|---|---|---|
| C-1 | 0.0065 | 2381.4 | 3.602 | | |
| C-2 | 0.0054 | 2195.3 | 3.221 | | |
| C-3 | 0.0056 | 2477.1 | 2.979 | | |
| C-4 | 0.0045 | 2189.3 | 2.737 | | |
| C-5 | 0.0049 | 1998.3 | 3.213 | | |
| C-6 | 0.0066 | 2255 | 3.88 | 3.272 | 0.41 |
| B-1 | 0.142 | 2188.3 | 85.69 | | |
| B-2 | 0.1757 | 3029.2 | 76.58 | | |
| B-3 | 0.0367 | 2304.1 | 21.02 | | |
| B-4 | 0.137 | 2176.8 | 83.1 | | |
| B-5 | 0.0412 | 3091.9 | 17.59 | 56.8 | 34.4 |
| A-1 | 0.0068 | 2188.8 | 4.083 | | |
| A-2 | 0.0084 | 2303.1 | 4.817 | | |
| A-3 | 0.0056 | 2171.8 | 3.382 | | |
| A-4 | 0.0073 | 2356.3 | 4.083 | | |
| A-5 | 0.0054 | 2579.4 | 2.761 | 3.825 | 0.78 |

TABLE 3

Cathepsin B + L

| Mouse | Δ AMC | Protein Conc. | Specific Activity | Mean | S.D. |
|---|---|---|---|---|---|
| C-1 | 0.1112 | 2381.4 | 61.64 | | |
| C-2 | 0.1276 | 2195.3 | 76.72 | | |
| C-3 | 0.11408 | 2477.1 | 60.79 | | |
| C-4 | 0.11685 | 2189.3 | 70.45 | | |
| C-5 | 0.1034 | 1998.3 | 68.31 | | |
| C-6 | 0.11234 | 2255 | 65.76 | 67.28 | 5.942 |
| B-1 | 0.90735 | 2188.3 | 547.3 | | |
| B-2 | 1.0155 | 3029.2 | 442.5 | | |
| B-3 | 0.30005 | 2304.1 | 171.9 | | |
| B-4 | 0.85004 | 2176.8 | 515.5 | | |
| B-5 | 0.26715 | 3091.9 | 114.1 | 358.2 | 201.2 |
| A-1 | 0.09708 | 2188.8 | 58.55 | | |
| A-2 | 0.13749 | 2303.1 | 78.8 | | |
| A-3 | 0.07708 | 2171.8 | 46.85 | | |
| A-4 | 0.08475 | 2356.3 | 47.48 | | |
| A-5 | 0.04716 | 2579.4 | 24.14 | 51.15 | 19.88 |

Although cathepsin B and cathepsin B+L activity were significantly increased in the comparison group, a level of activity in the test group was almost same as that of the control group.

Experiment 3

The animals were kept and managed in the same manner as Experiment 1, gastroenemius muscle was obtained in the same manner, frozen cross-sections of said gastroenemius muscle were prepared to a thickness of 4 μm, and the sections were placed on slide glasses coated with poly-L-lysine. One of the slide glasses was stained with hematoxylin and eosin stain.

For the other glass slides, after blocking intrinsic peroxidase for 20 minutes in 0.1% (w/v) sodium azide containing 0.3% (v/v) hydrogen peroxide, the slides were treated for 20 minutes with 3% (v/v) normal goat serum to block any non-specific bonding. The sections were then incubated overnight in a humidified room at 4° C. with purified rabbit antibody to rat cathepsin B (Kominami, E., et al., J. Biochem., 98, 87–93, 1985) (2 μg/ml) and rabbit antibody to rat cathepsin L (Banco, Y. et al., J. Biochem., 100, 35–42, 1986) (10 μg/ml).

After washing in PBS, mouse anti-rabbit immunoglobulin conjugated with biotin (Histofine SAB-PO kit, Nichirei Co., Ltd.) was added after which the slides were incubated for 20 minutes at room temperature. After thoroughly washing in PBS, streptoavidine conjugated with peroxidase was added after which the slides were additionally incubated for 20 minutes.

The immunostained products were developed by allowing to react for 3 minutes with 0.02% (w/v) 3,3'-diaminobenzidine and 0.03% (v/v) hydrogen peroxidase in 0.05 M Tris-HCl (pH 7.6). Each staining test contained a negative control using normal goat serum. Those results are shown in FIG. 1 through 6. Cathepsin B and L were strongly stained in the IL-6 transgenic mice. On the other hand, expression of cathepsin B and L was inhibited in the transgenic mice administered with IL-6 receptor antibody.

Experiment 4

The animals were kept and managed in the same manner as in Experiment 1. Ten of the above-mentioned normal mice were used for the control group, while 10 of the above-mentioned transgenic mice were used for the test group. Total RNA was extracted from the gastroenemius muscle using guanidine thiocyanate according to the method of Chirgwin, J. M. et al., Biochemistry 18, 5291–5301, 1979, which was then quantified according to the optical density at 260 nm.

A 10 μg sample of RNA was applied to electrophoresis in 1.0% agarose gel containing formaldehyde, after which the RNA was plotted overnight on a high-bond Nylon membrane (Amersham) using 20x standard salt citrate solution (SSC: 0.15 M NaCl and 15 mM sodium citrate, pH 7.0). The RNA in the gel and filter was visualized with ethidium bromide and photographs were taken by UV transillumination to confirm that equal amounts of RNA had been transcribed.

Figure 7:
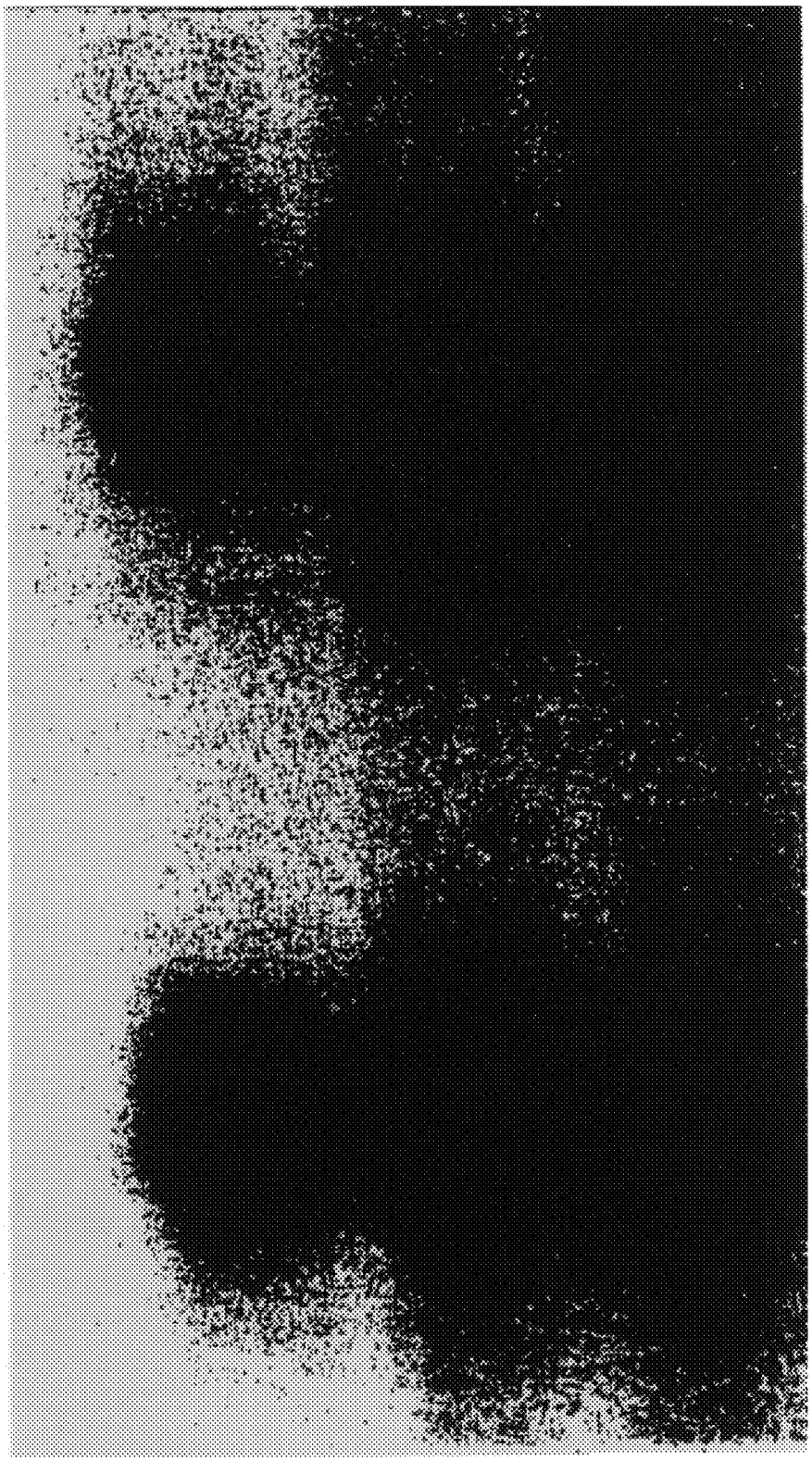
FIG. 7 is a photograph that shows the results of northern hybridization on RNA originating in gastroenemius muscle of (A) a control mouse, (B) a transgenic mouse administered PBS, and (C) a transgenic mouse administered IL-6 receptor antibody, using polyubiquitin cDNA for the probe.
Figure 8:
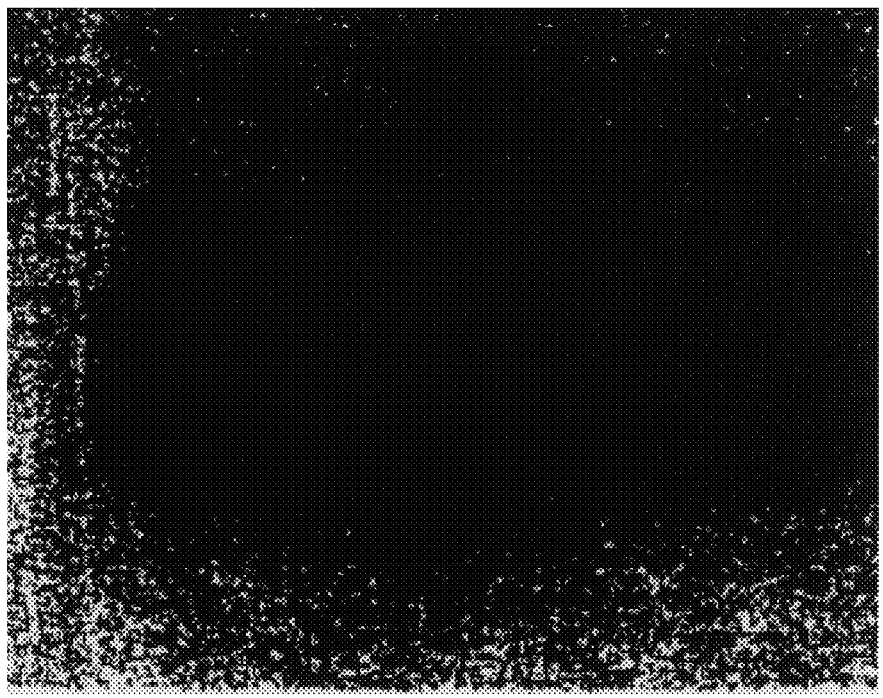
FIG. 8 is a photograph that shows the results of northern hybridization on RNA derived from gastroenemius muscle of (A) a control mouse, (B) a transgenic mouse administered PBS, and (C) a transgenic mouse administered IL-6 receptor antibody, using monoubiquitin cDNA for the probe.

Radioactively labeled probes were prepared according to the random primer method using cDNA coding for poly-ubiquitin (poly-Ub) and cDNA coding for monoubiquitin (mono-Ub) (Kanayama, H. et al., Cancer Res., 51, 6677–6685, 1991). After pre-hybridizing the above-mentioned membrane for 1 hour, it was hybridized with the above-mentioned probes overnight using Church buffer. The filter was exposed to Kodak XAR-5 film for 1 to 3 hours at −80° C. using a reinforced screen. The images on the film were then quantified with a densitometer using an MCID system (Imaging Research Inc., Ontario, Canada). Those results are shown in FIGS. 7 and 8. Expression of RNA was enhanced in the transgenic mice for both poly-Ub and mono-Ub, and expression of RNA was inhibited in the group administered IL-6 receptor antibody.

Example 2

The inhibitory effect on muscle protein proteolysis by IL-6 receptor antibody in colon 26 tumor-bearing mice was studied. Male BALB/c mice 6 weeks old were used in the study, and colon 26 was transplanted subcutaneously into the flank of the mice on the day the experiment was started. Mouse IL-6 receptor antibody MR16-1 (see Reference Example 2) was administered subcutaneously at 0.5 mg/mouse on days 4, 6, 8, 10, 12, 14 and 16 after transplantation of colon 26 on the day the experiment was started. In this method, it had been confirmed in previous experiments that there is little appearance of neutralizing antibody to rat antibody of heterogeneous protein. Furthermore, rat IgG (KH5) was administered according to the same schedule to both a tumor-bearing control group (n=7) and a non-tumor-bearing control group (n=7).

The animals were observed for body weight including tumor weight, body weight excluding tumor weight (carcass weight) and gastroenemius muscle weight on day 17 after the start of the experiment, and the cathepsin B and cathepsin B+L activity of gastroenemius muscle were also assayed. Furthermore, assay of cathepsin B activity and cathepsin B+L activity was performed in the same manner as the above-mentioned Experiment 2.

Figure 9:
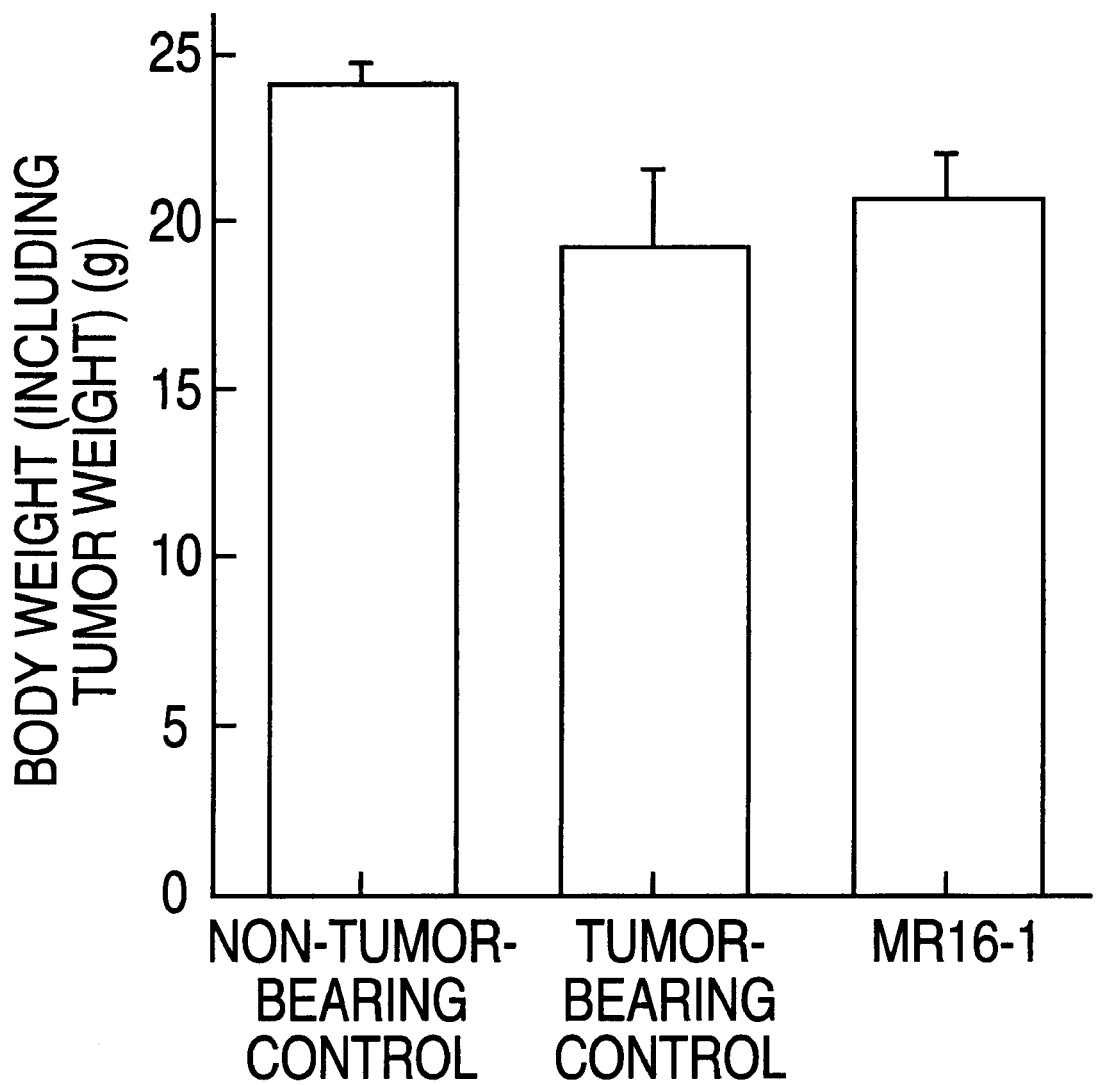
FIG. 9 is a graph indicating the body weights of mice on experiment day 17, including tumor weights.
Figure 10:
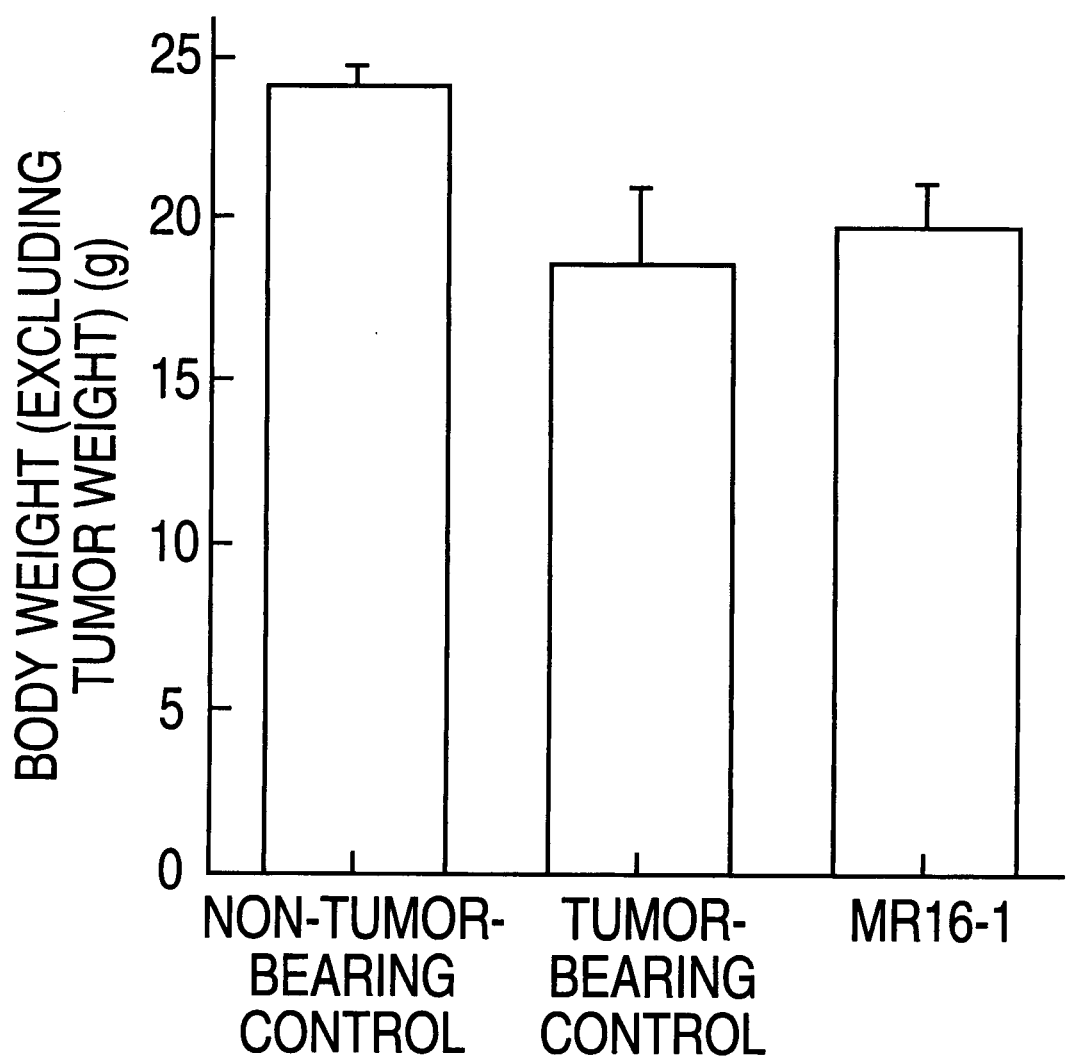
FIG. 10 is a graph indicating the carcass weights of mice on experiment day 17, not including tumor weights.
Figure 11:
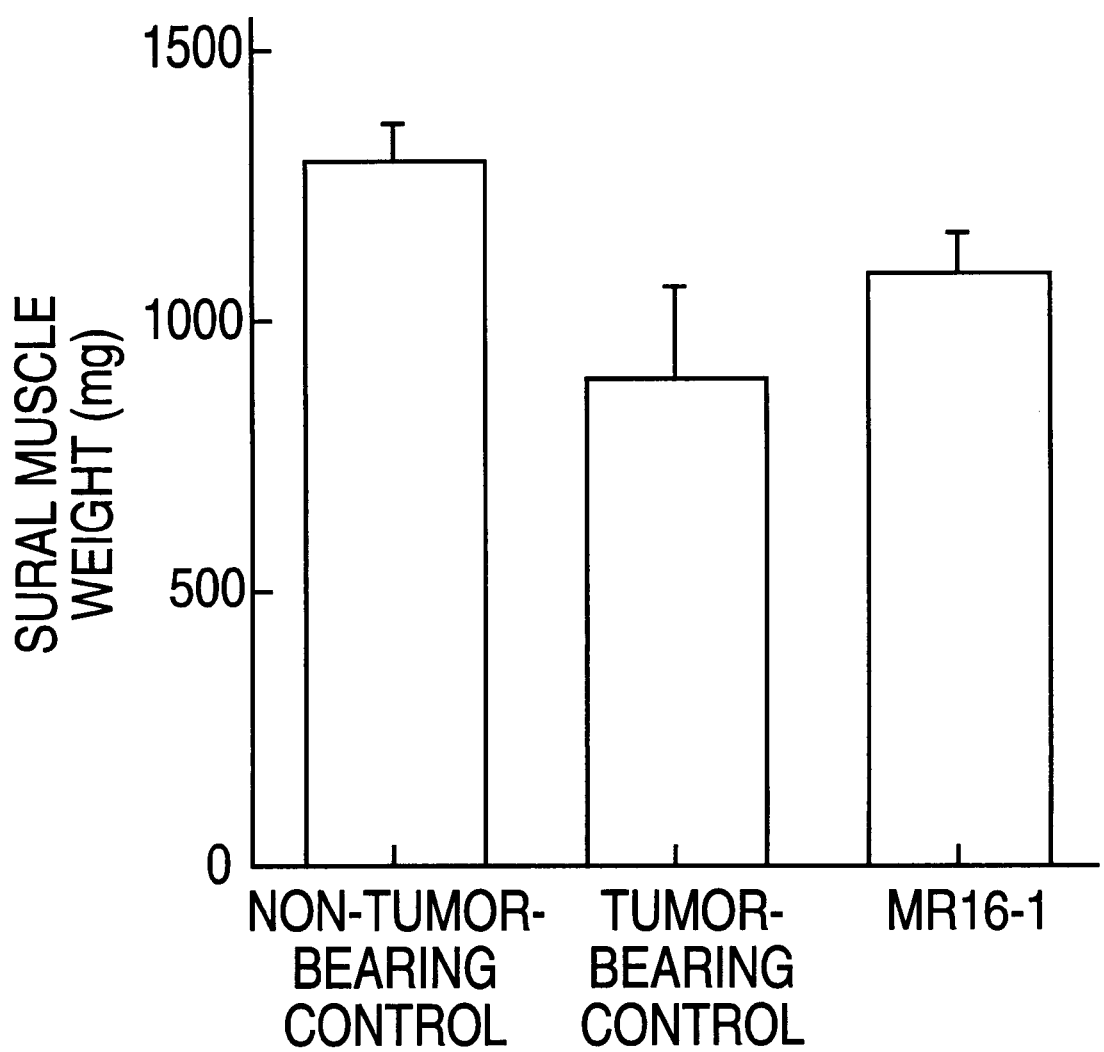
FIG. 11 is a graph indicating gastroenemius muscle weight of mice on experiment day 17.

Body weight including tumor weight, body weight excluding tumor weight (carcass weight) and gastroenemius muscle weight on day 17 after the stat of the experiment are shown in FIGS. 9, 10 and 11, respectively. Decreases in carcass weight and gastroenemius muscle weight were inhibited in the IL-6 receptor antibody administration group (there were no significant differences in body weight including tumor weight).

Figure 12:
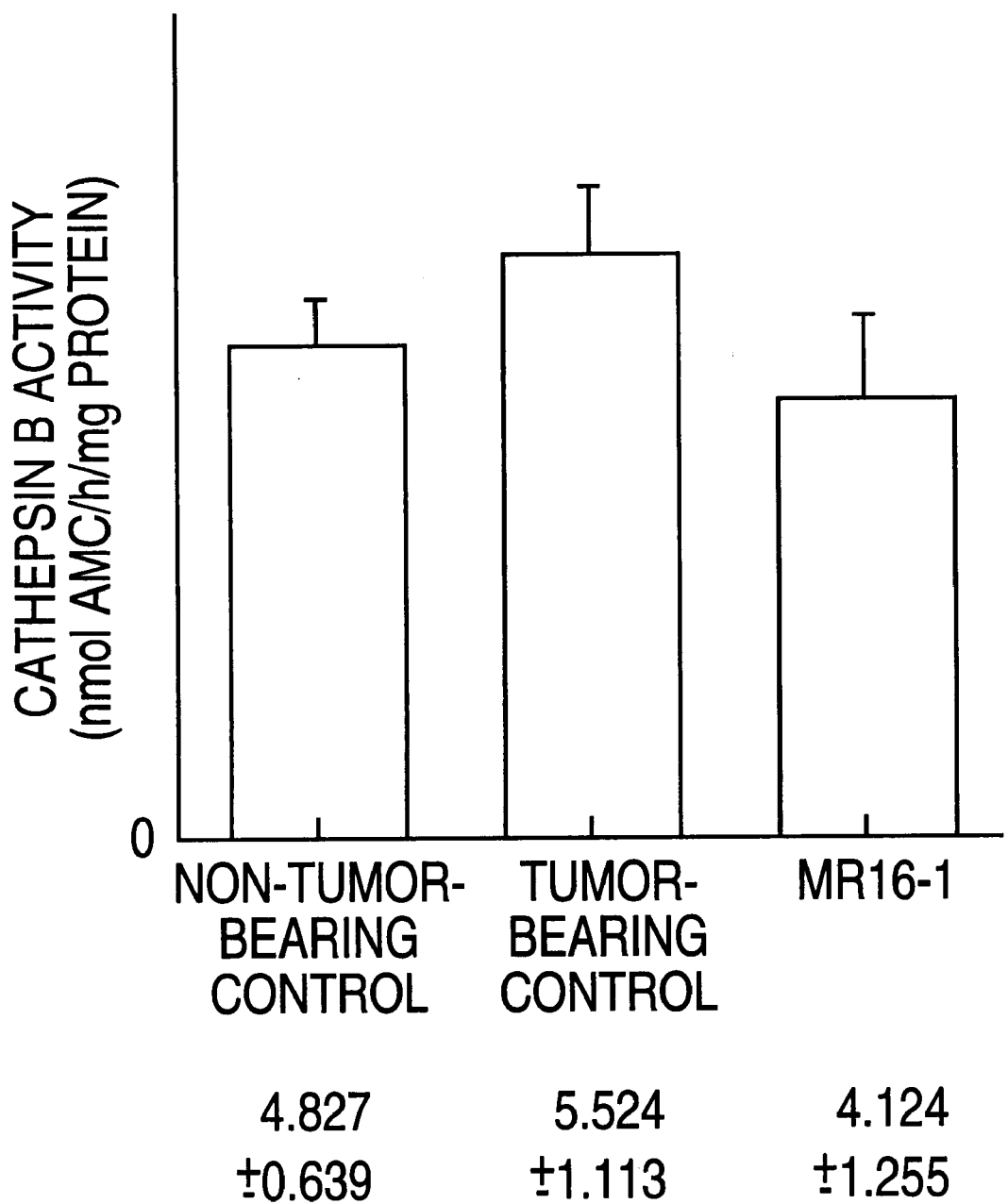
FIG. 12 is a graph indicating cathepsin B activity in mouse gastroenemius muscle on experiment day 17.

Cathepsin B activity and cathepsin B+L activity on day 17 of the experiment are shown in FIGS. 12 and 13, respectively. Increases in cathepsin B activity and cathepsin B+L activity observed over time were inhibited by administration of IL-6 receptor antibody (there were no significant differences observed regarding cathepsin B activity).

Industrial Applicability

IL-6 is involved in the breakdown of skeletal muscle mediated by proteolytic enzyme systems. Since inhibitory effects on muscle protein proteolysis were observed to be exhibited by IL-6 receptor antibody, the present invention is suggested to be useful as an inhibiting agent of muscle protein proteolysis.

What is claimed is:

1. A method for inhibiting the expression, the activity or a combination thereof, of at least one proteolytic enzyme that promotes muscle protein proteolysis comprising the step of administering a neutralizing antibody to an interleukin-6 receptor to a patient in need of the inhibition of the expression, activity or a combination thereof, of at least one proteolytic enzyme that promotes muscle protein proteolysis, wherein said neutralizing antibody inhibits the biological activity of interleukin-6 inhibiting binding between IL-6 and IL-6 receptor.

2. The method of claim 1, wherein said proteolytic enzyme is at least one of cathepsin, polyubiquitin or monoubiquitin.

3. The method of claim 2, wherein said proteolytic enzyme is at least one of Cathepsin B or Cathepsin L.

4. The method of claim 1, wherein said interleukin-6 receptor is a human interleukin-6 receptor.

5. The method of claim 1, wherein said antibody to said interleukin-6 receptor is a monoclonal antibody.

6. The method of claim 5, wherein said antibody to said interleukin-6 receptor is MR16-1.

7. The method of claim 5, wherein said antibody to said interleukin-6 receptor is PM-1.

8. The method of claim 5, wherein said antibody to said interleukin-6 receptor is a humanized PM-1.

9. The method of claim 2, wherein said antibody to said interleukin-6 receptor is a monoclonal antibody.

10. The method of claim 9, wherein said antibody to said interleukin-6 receptor is MR16-1.

11. The method of claim 9, wherein said antibody to said interleukin-6 receptor is PM-1.

12. The method of claim 9, wherein said antibody to said interleukin-6 receptor is a humanized PM-1.

13. The method of claim 1, wherein the expression, the activity or a combination thereof, of at least one proteolytic enzyme that promotes muscle protein proteolysis occurs in association with cancerous cachexia.

* * * * *

SEQUENCE LISTING (1) GENERAL INFORMATION:

(iii) NUMBER OF SEQUENCES: 2

```
(2) INFORMATION FOR SEQ ID NO:1:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA"

(xi) SEQUENCE DESCRIPTION: SEQ ID NO:1:

ACCTCTTCAG AACGAATTGA CAAA                                              24

(2) INFORMATION FOR SEQ ID NO:2:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA"

(xi) SEQUENCE DESCRIPTION: SEQ ID NO:2:

AGCTGCGCAG AATGAGATGA GTTGT                                             25
```